United States Patent [19]

Ferguson

[11] Patent Number: 4,664,661
[45] Date of Patent: May 12, 1987

[54] MODIFIED ACCORDION FLANGE

[75] Inventor: Keith T. Ferguson, Scotch Plains, N.J.

[73] Assignee: E. R. Squibb & Sons, Inc., Princeton, N.J.

[21] Appl. No.: 641,642

[22] Filed: Aug. 17, 1984

[51] Int. Cl.⁴ ............................................. A63F 5/44
[52] U.S. Cl. ................................... 604/342; 604/344
[58] Field of Search ................ 128/156; 131/243, 247; 604/343, 304, 332, 339, 333, 336, 338, 341, 342, 344; 220/306, 307, 276, 325

[56]  References Cited
U.S. PATENT DOCUMENTS 3,339,546  9/1967  Chen .
4,213,458  7/1980  Nolan et al. .
4,419,100  12/1983  Alexander .

FOREIGN PATENT DOCUMENTS 98718  6/1983  European Pat. Off. ............ 604/343
1571657  7/1980  United Kingdom .

Primary Examiner—Richard C. Pinkham
Assistant Examiner—T. Brown
Attorney, Agent, or Firm—Lawrence S. Levinson; Robert E. Lee, Jr.

[57]  ABSTRACT

An ostomy device for releasably connecting an ostomy bag to an adhesive backed label including a mounting member for connecting one of two coupling parts to the label. The mounting member comprises an expandable portion for facilitating displacement of the connected coupling part between a normal closed position and an expanded position. The expanded portion comprises a pair of accordion-like folds including an inner fold and a smaller outer fold. The connected coupling part comprises a rib portion having a deflectible sealing strip extending therefrom. The rib portion is connected to the mounting member adjacent the outer folds such that the sealing strip is positioned intermediate the inner and outer folds when the coupling part is in the normal closed position. The inner fold guides discharge from the stoma into the bag and away from the interengaged coupling parts. In an alternate embodiment, the mounting member is affixed to the label.

8 Claims, 8 Drawing Figures

MODIFIED ACCORDION FLANGE

BACKGROUND OF THE INVENTION

The present invention relates to an ostomy bag and to an improved coupling for joining an ostomy bag to a pad, label or surgical dressing.

Ostomy bags are used to collect waste from patients with a stoma resulting from an ileostomy, colostomy or similar surgical procedure. An ostomy bag comprises two thin film walls which are sealed along their periphery by heat welding or the like. One wall has an aperture to receive the stoma.

The ostomy bag is secured to the patient by attaching it to an adhesive backed label through which an opening can be made in the center to receive the stoma. The adhesive backed label can be worn comfortably for extended periods of time which are longer than the time normally required for the bag to fill to capacity with waste material. Examples of acceptable adhesive backed labels are described in U.S. Pat. No. 3,339,546 by Chen.

It is desirable when replacing the filled ostomy bag with an empty one that the ostomy bag be removed and replaced without requiring that the adhesive backed label be removed. This is accomplished through the use of a coupler which comprises a pair of plastic rings, one of which forms a channel or groove and the other, a projection or rib for frictional engagement with the channel or groove. Each ring defines an aperture for receiving a stoma therethrough. One ring, usually the one with the channel, is attached to the bag with its aperture aligned with the aperature in the bag, while the other ring is attached to the label on a surface opposite the adhesive, also with its aperture aligned with the opening in the bag when the two rings are coupled together. Using this coupling arrangement the bag and label can be connected around the stoma by aligning the coupler rings and pressing them together to cause frictional engagement. A coupler suitable for this application is described in Great Britain patent specification No. 1,571,657, published July 16, 1980.

The coupling rings are coupled together by applying a significant force on the bag to press the rings together. Where one of the coupling rings is mounted directly to the surface of the label, a great amount of the force is absorbed by the sensitive skin beneath the label. In the prior art to reduce the force applied to the skin, an outwardly extending flange portion of the ring to be attached to the label is attached along a portion of its bottom surface to an outer edge portion of a thin annular web of flexible thermoplastic material. The web extends inwardly from the flange portion and the inner edge portion of the web is attached to the label. This arrangement allows a user of the ostomy bag to insert the user's fingers between the web and the label and press the coupling rings together to attach the ostomy bag to the label. The fingers then absorb at least some of the applied force. See U.S. Pat. No. 4,419,100. This patent further discloses that the inner edge of the web may be attached to an annular mounting collar which in turn is attached to the faceplate to reinforce it in the area about the opening which receives the stoma. See 30a in FIG. 2.

In European patent application No. A10098718 published Jan. 18, 1984, a ring mounting means for mounting a coupling ring to the label is disclosed which includes a first section adapted to be affixed to the surface of the label and an accordion-like section positioned between the first section and a second section to be attached to the coupling ring. The accordion-like sections facilitate displacement of the coupling ring from the label so that the coupling rings can be engaged and the force diverted from the skin around the stoma by permitting the mounting means to expand when the fingers are inserted between the coupling ring and the label. Accordion-like sections with a single fold and triple folds are explicitly disclosed. The single fold is higher to provide the same amount of movement away from the label as the triple fold design, but has the disadvantage of providing a higher profile. Also, the single fold design places more stress on the single hinge at the fold sometimes resulting in cracking at the fold.

The second section is attached to the coupling ring along a base or bottom portion thereof. When the coupling ring includes an annular rib or protrusion for frictional engagement with a groove in the other coupling ring, the second section is attached to the underside of the outwardly extending flange portion of the ring, or if there is no flange to the rear surface of the protrusion of the coupling ring.

In general, the first section of the mounting means is affixed by heat or sonic weld along an annular region to the label surface. The annular region defines an opening to receive the stoma which opening has a diameter or dimensions which are smaller than the apertures in the rings or bag. This is particularly true where the accordion-like folds are disposed in a direction parallel to the surface of the label.

When designing the mounting means for attaching a coupling ring such as the coupling rings described above it is desirable to provide maximum flexibility, low profile, and comfort of use, while insuring adequate support for the ostomy bag during use and secure and reliable attachment of the mounting means to the label. At the same time it is desirable to maximize the area of the opening defined by attachment of the mounting means to the label for receiving the largest size stoma possible. Further it is desirable that the coupling and mounting means guide the discharge from the stoma into the bag and prevent the flow of discharge along the surface of the label.

SUMMARY OF THE INVENTION

The present invention relates to an ostomy device for releasably connecting an ostomy bag to an adhesive backed label. The ostomy device comprises a mounting member for connecting one of two closed loop coupling parts to the label. The mounting member includes an expandable portion connected between the label and the coupling part which comprises a pair of accordion-like folds, an inner fold and a smaller outer fold. The expandable member facilitates displacement of the connected ring between a normal position and an expanded position spaced apart from the label.

In the preferred embodiment one of the coupling rings comprises a rib portion having a sealing strip extending therefrom. The rib portion is affixed to a portion of the mounting member adjacent the smaller outer fold such that the sealing strip is positioned intermediate the inner and outer folds when the coupling ring is in the normal position.

The other coupling part comprises two opposed walls adapted to receive the rib portion and sealing strip therebetween. When the two coupling parts are coupled and in the normal position, the inner folds overlaps the inner wall. The inner fold guides discharge from a stoma into the ostomy bag and away from the coupled parts.

The mounting member further comprises a portion which extends outwardly from the stoma past the connected coupling part to form a soft flange. The soft flange facilitates coupling and decoupling and is more comfortable to wear than prior art thicker flanges.

An alternate embodiment ostomy device further includes a lower annular ring. An inner edge portion of the mounting member is affixed to an inner edge portion of the ring which is then affixed to a thin plastic surface of the label. The inner edge portions are adapted to form a maximized stoma aperture. In the preferred embodiment, the mounting member is heat molded to the ring. The annular ring is provided with a hot melt adhesive layer for affixing the annular ring to the label.

In general, the plastic surface of the label is made of a low density polyethylene as are the mounting member and annular ring. However, the thickness of the plastic surface is usually substantially thinner than either the mounting member or the annular ring.

DETAILED DESCRIPTION OF THE DRAWINGS

Figure 1:
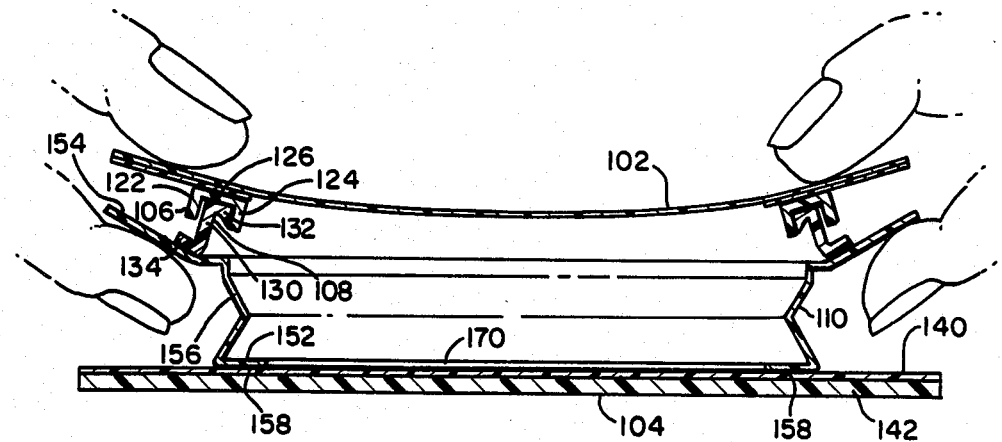
FIG. 1 is a cross-sectional view of one embodiment of the present invention ostomy device shown in an expanded position.
Figure 2:
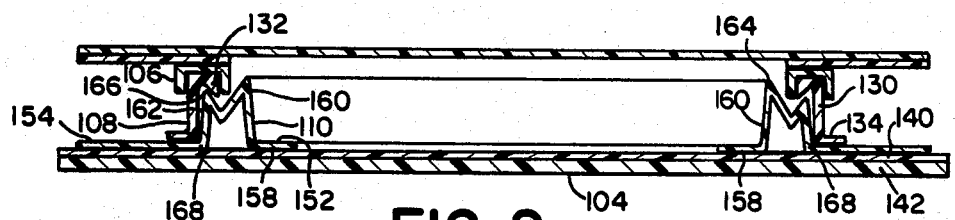
FIG. 2 is a cross-sectional view of the ostomy device of FIG. 1 shown in a normal position for use.

FIGS. 1 and 2 illustrate an ostomy device designated generally 100 of the present invention comprising an ostomy bag 102, an adhesive backed label 104 suitable for use on a patient's skin, first and second coupling rings 106 and 108 shown in frictional engagement, and a mounting means 110 for mounting one of the first or second rings 106 or 108, respectively, to the label 104. The mounting means coupling rings and label are shown in cross-section. The first coupling ring 106 is shown attached to one side 120 of ostomy bag 102. Side 120 of ostomy bag 102 has an aperture therein to receive a stoma and coupling ring 106 is circular also defining an aperture. Ring 106 is positioned such that the aperture it defines is aligned with the bag aperture to receive the stoma. Coupling ring 106 is preferably a deformable but resilient plastic material and comprises a channel formed by opposing walls 122 and 124 integrally connected together by base 126. The base 126 of coupling ring is secured to the bag by adhesive or heat welding for example.

Second coupling ring 108, also preferably made from a resilient and deformable plastic material and circular in shape to define an aperture comprises a rib portion 130, a deflectable sealing strip 132 and a base 134. The coupling members are adapted to be frictionally engaged by pressing them together, the rib portion 130 into the channel of the opposing coupling ring. When so engaged, the deflectable stealing strip 132 engages the surface of the wall and the aperture defined by ring 108 is aligned with the apertures of ring 106 and bag 102.

Either or both of coupling rings 106 and 108 may be injection molded from any suitable synthetic plastics material which may but need not be of low density polyethylene.

The purpose of the adhesive backed label 104 is to attach the ostomy device 100 to the skin of the wearer. Label 104 comprises a base 140 which is preferably a thin film of polymeric material such as polyethylene and an adhesive layer 142 situated on the rear surface of base 140. Adhesive layer 142 is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents.

The second coupling ring with circular rib portion 130 is attached or mounted to the thin film of polymeric material of base 140 of label 104 by member 110. Member 110 comprises first section 152, flange portion 154 and expandable section 156 connecting the first section 152 to the flange portion 154. Member 110 is preferably made of plastic or similar material, such as polyethylene, which is of sufficient strength and thickness to maintain the bag in a normal position proximate the surface of label 104 even when the bag is filled with waste material.

Figure 3:
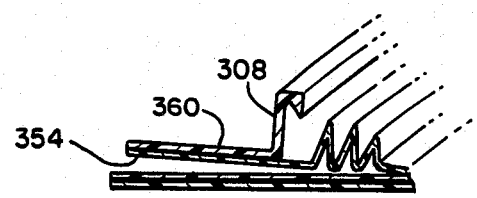
FIG. 3 is an oblique view of a portion of a prior art ostomy bag coupling ring, mounting member and adhesive backed label.

The first section 152 in FIGS. 1-3 is attached by heat or sonic welding or adhesive to the base 140 along an annular region 158 which defines an opening to receive the stoma. The diameter or dimensions of the opening are less than the apertures defined by the ring members 106 and 108.

The expandable section 156 comprises a pair of accordion-like folds 160 and 162 located between sections 152 and 154 and disposed in a direction parallel to the surface of label 104. Folds 160 and 162 facilitate displacement of the second coupling ring 108 relative to the surface of base 140 by permitting the member 110 to expand when fingers are inserted between the member 110 and the label 104. By using two folds, the profile of the couplings is less than with one fold and less stress is borne by the hinges created at the fold peaks. At the same time two folds allow the opening created by the annular sealing region 158 to be larger than with a three fold arrangement since less space is required between the annular region 158 and attachment to ring member 108 when two folds are used rather than three folds.

In the preferred embodiment the height of peak 164 of inner fold 160 is higher than the height of peak 166 of outer fold 162 when the connecting members are in the closed position as in FIG. 2. The member 110 is attached by heat welding or adhesive to the bottom of base 134 of the second coupling member 108 at the juncture 168 of the outer leg of fold 162 with flange portion 154 such that as the connecting member 110 is folded into the closed position as in FIG. 2, at least a portions of the deflectable sealing member 132 passes over the lower peak 166 to become positioned intermediate peaks 166 and 164. This arrangement provides for a compact design allowing the diameter of the annular sealing region 158 to be enlarged even more.

It should also be noted that the peak 164 of inner fold 160 extends slightly above the end of inner channel wall 124 when the coupling rings are connected and are in the closed position. This aids in guiding discharge from the stoma into the bag and aids in preventing discharge from flowing laterally into the engagement area of the rib projection 130 with the channel walls 122 and 124.

Flange portion 154 extends outwardly beyond the base 134 to facilitate insertion of the fingers between the member 110 and label 104. In some prior art arrangements, the outwardly extending flange portion 154 is attached by heat welding or adhesive to the underside of a flange portion of the ring member. For example, in FIG. 3 see the flange portion 354 of the mounting member attached to the flange portion 360 of the ring member 308. However, with the arrangement of FIG. 3, the double thickness of the flange creates a stiffer flange which can cause some discomfort to the wearer as the wearer moves about. With the flange 154 of FIG. 2, and terminated base 134 of FIGS. 1 and 2, the flange is softer and more flexible lending more comfort to the wearer.

Figure 4:
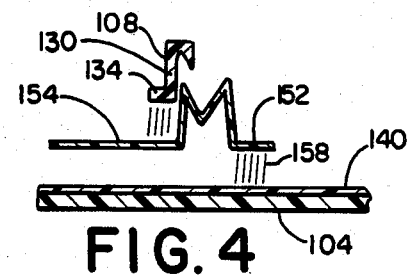
FIG. 4 is an exploded cross-sectional view of a portion of the ostomy device of FIGS. 1 and 2.

FIG. 4 shows the steps of a first method of connecting a coupling ring (such as coupling ring 108) to mounting member 110 and then connecting the assembly to the polyethylene base surface 140 of label 104. For example, the base 134 is first heat welded to the second section or flange 154 of the mounting member 110. Because the mounting member 110 and coupling ring 108 are made of the same material (for example, low density polyethylene with substantially the same thickness) the bond formed between them by heat welding is extremely strong.

Following assembly of the coupling ring and mounting member, the first section 152 of mounting member 110 is connected to the thin polyethylene base 140 of label 104 along circular region 158. This is done usually by sonic welding. It is desirable to make first section 152 as short as possible so as to maximize the opening 170 formed by region 158. This allows for a larger stoma. However, because of the thinness of base layer 104 the size of annular region 158 is larger than it might otherwise be. For example, using sonic welding with a label having a base layer 2 mils thick requires at least a 250 mils long first section 152 to insure secure mounting of the assembly to the label during continual use.

Figure 5:
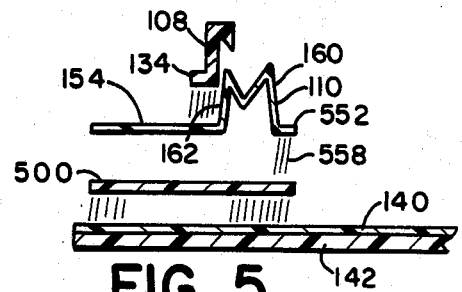
FIG. 5 is a cross-sectional view of an alternate embodiment of the present invention ostomy device shown in an expanded position.

FIG. 5 shows an improved method of assembly and mounting which results in an improved ostomy device. In FIG. 5, the base 134 is heat welded as before to the flange 154 of mounting member 110. Then a first section 552 of mounting member 110 is heat welded to a circular lower ring 500. A hole punch operation is performed to form a maximized aperture 570 (see FIGS. 6 and 7) through the lower ring 500 and first section 552. This leaves a smaller annular bonding region 558 between the inner edge of lower ring 500 and the shortened first section 552 than the annular bonding region 158 formed between the first section 152 and surface 140 of label 104 formed by a knurled sonic welding operation as in FIGS. 1, 2 and 4.

As a final step the lower ring 500 is bonded to the label surface 140 using a hot melt adhesive process where the hot melt adhesive is applied to the bottom of the lower ring 500. By using the lower ring, the bond between the mounting member 110 and label 104 is transferred from the narrow region 558 to the large surface below the lower ring.

The above described method described in connection with FIG. 5 is less expensive than that associated with FIG. 4. The lower ring can be made from roll stock, welded to the mounting member and cut without additional equipment. Substantial savings will be provided by replacing the existing sonic knurl weld with a faster adhesive bonding operation.

The use of a lower ring per se is not new. In FIGS. 12 and 13 of U.S. Pat. No. 4,213,452, for example, the inner side of an attaching ring 31' made of polyethylene is heat sealed in an annular area to a side 17' of a thermoplastic ostomy bag around a bag opening 22'. The outer side of attaching ring 31' supports an outer layer 40' of a hot melt adhesive. The inner side of a microporous adhesive patch 34' is heat sealed fused to the outer side of attaching ring 31' by means of hot melt adhesive layer 40'.

There is no teaching however of the above described method of the present invention described in connection with FIG. 5 for optimizing the usable area in the center of the label for receiving a stoma.

Figure 6:
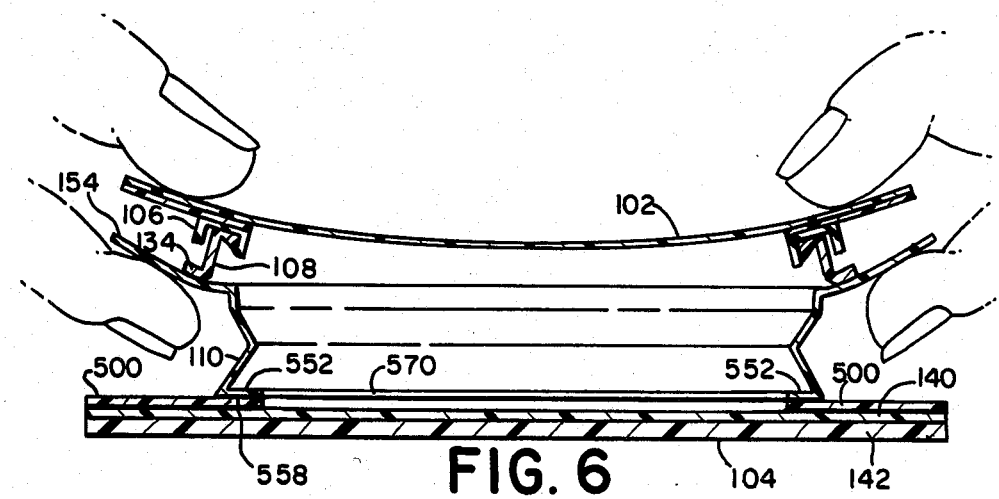
FIG. 6 is a cross-sectional view of the alternate embodiment ostomy device of FIG. 5 shown in a normal position for use.
Figure 7:
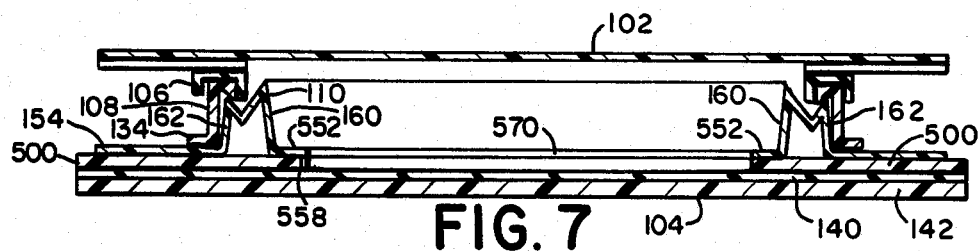
FIG. 7 is an exploded cross-sectional view of a portion of the ostomy device of FIGS. 5 and 6.

FIGS. 6 and 7 show an ostomy device using the lower ring 500 described above. FIG. 6 shows the coupling rings 106 and 108 attached with the mounting member 110 in the expanded position while FIG. 7 shows the mounting member in the closed position.

Figure 8:
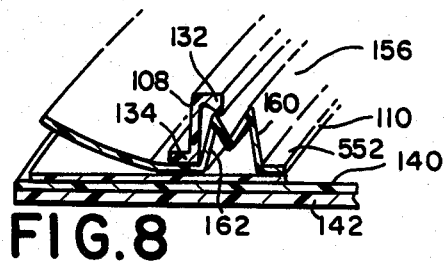
FIG. 8 is an oblique view of a portion of the ostomy device of FIGS. 5 and 6.

Referring to FIGS. 6, 7 and 8, by mounting the shortened base 134 of coupling ring 108 adjoined to the smaller fold 162 of the two fold accordion section 156 of mounting member 110 such that the sealing strip 132 falls between the peaks of the two folds with mounting member 110 heat welded along the annular region formed between shortened section 552 and lower ring 500 which in turn is affixed to base 140 with a hot melt adhesive an optimized size opening area on the label is formed for receiving the largest size stoma possible. The higher peak of inner fold 160 provides a means for reducing the flow of discharge from the stoma intot the engagement area of the coupling rings 106 and 108, while the single thickness flange formed by the flange 154 of mounting member 110 provides a means for engaging and disengaging the coupling rings which is comfortable for the wearer.

What is claimed is:

1. An ostomy device including a bag, an adhesive-backed label and means for releasably connecting said bag and label, said connecting means further comprising first and second interengaging parts, each of closed loop form for defining a stoma aperture therein, said first part coupled to said bag, said connecting means further comprising mounting means for mounting said second part on said label, said mounting means comprising:
    a first section coupled to said label along an annular region defining a stoma aperture therein;
    a second section affixed to said second part; and
    an expandable member connected between said first and second sections for facilitating displacement of said second part between a normal closed position and an expanded position spaced apart from said label, said expandable member comprising:
    a pair of accordian-like folds including an inner fold and a smaller outer fold, said second part comprising:
    a rib portion including a thin resilient deflectable sealing strip extending from said rib portion, said rib portion affixed to said second section adjacent an outer wall of said smaller outer fold such that said sealing strip is positioned intermediate said inner and outer folds when said second part is in said normal closed position.

2. The device of claim 1 wherein said first part comprises two opposed walls adapted to receive said rib portion and sealing strip therebetween when said first and second parts are interengaged, and said inner fold is adapted to overlap the inner one of said two opposed walls when said first and second parts are interengaged and disposed in said normal position.

3. The device of claim 1 wherein said second section extends outwardly from said second part to form a soft flange.

4. The device of claim 1 wherein said first section is affixed directly to said label along said annular region.

5. The device of claim 1 wherein said device further comprises a lower annular ring affixed to said label defining said stoma aperture therein and wherein said first section is affixed to said lower annular ring along inner edge portions.

6. The device of claim 5 wherein said lower annular ring comprises a layer of hot melt adhesive for affixing said lower annular ring to said label.

7. The device of claim 6 wherein said first section is heat welded to said lower annular ring along said concentric inner edge portion.

8. The device of claim 5 wherein said second section extends outwardly from said second part to form a soft flange.

* * * * *